(12) United States Patent
Cherek et al.

(10) Patent No.: US 6,853,701 B2
(45) Date of Patent: Feb. 8, 2005

(54) COMPUTED TOMOGRAPHY SCANNING METHOD AND APPARATUS WHEREIN EXPOSURE OF AN EXAMINING PERSON TO SCANNING RADIATION IS AVOIDED

(76) Inventors: Dieter Cherek, Hirschaid (DE); Robert Kagermeier, Nuremberg (DE); Donal Medlar, Weisendorf (DE); Uwe Urmoneit, Gerhardshofen (DE)

(*) Notice: Subject to any disclaimer, the term of this patent is extended or adjusted under 35 U.S.C. 154(b) by 233 days.

(21) Appl. No.: 10/223,911

(22) Filed: Aug. 20, 2002

(65) Prior Publication Data
US 2003/0043956 A1 Mar. 6, 2003

(30) Foreign Application Priority Data
Aug. 20, 2001 (DE) .......................................... 101 40 740

(51) Int. Cl.⁷ .............................................. G01K 23/00
(52) U.S. Cl. ............................................ 378/16; 378/4
(58) Field of Search ........................................ 378/4, 16

(56) References Cited

U.S. PATENT DOCUMENTS

| 5,867,555 A | 2/1999 | Popescu et al. |
| 5,873,826 A | 2/1999 | Gono et al. |
| 6,501,820 B2 * | 12/2002 | Guendel .................... 378/15 |

* cited by examiner

*Primary Examiner*—Craig E. Church

(57) ABSTRACT

In a CT scanning method and apparatus wherein a radiation source is displaced around a system axis and a ray bundle therefrom strikes a detector system that supplies scan data on the basis whereof two-dimensional scan images of the examination subject are determined in an image calculating device, parameters describing the position of a body part of an examining person situated in the beam path are determined by an analysis of registered scan images, and the radiation source is controlled dependent on the analysis result so that the radiation is reduced when the body part is located in the beam path.

42 Claims, 1 Drawing Sheet

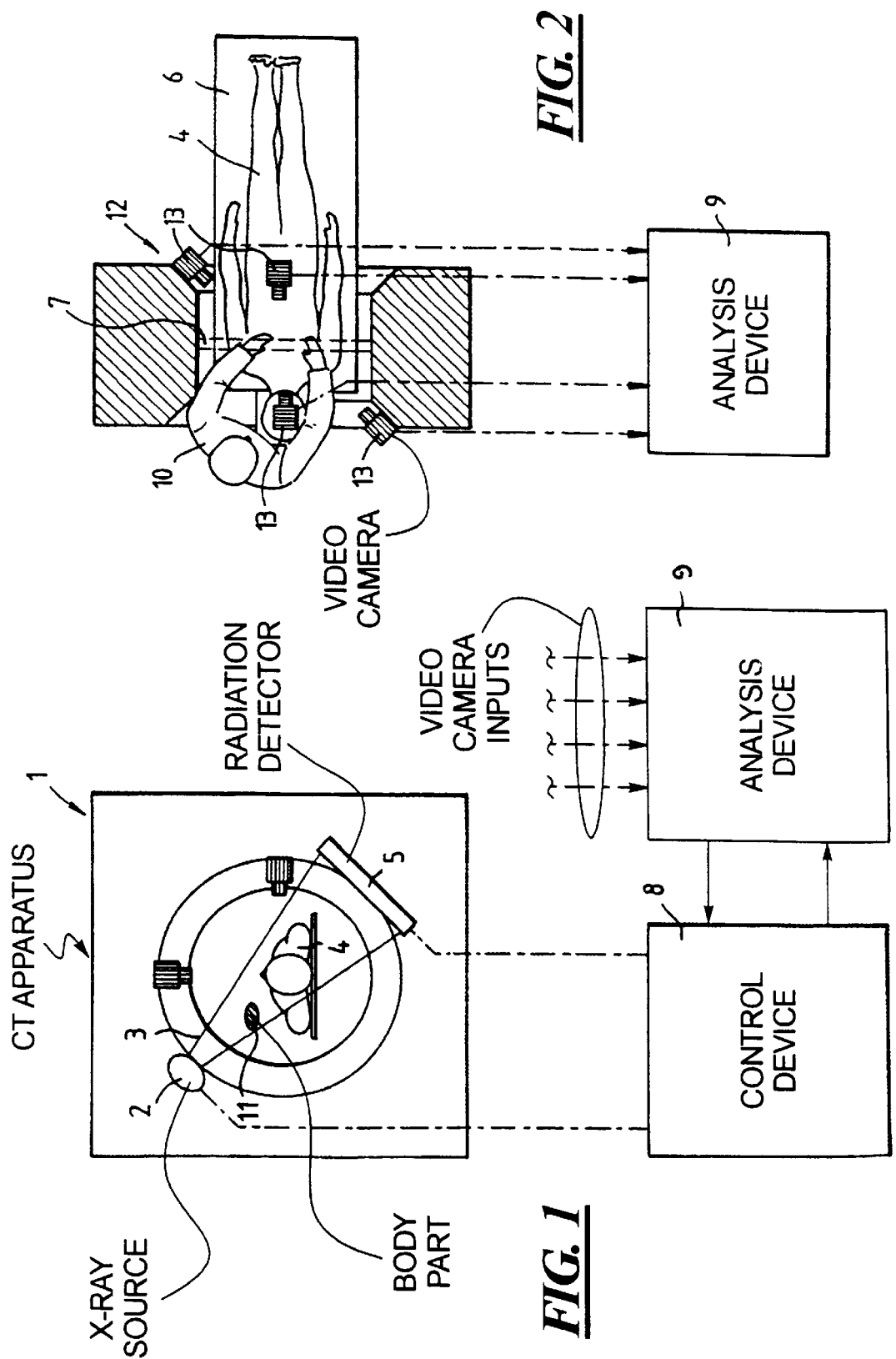

US 6,853,701 B2

COMPUTED TOMOGRAPHY SCANNING METHOD AND APPARATUS WHEREIN EXPOSURE OF AN EXAMINING PERSON TO SCANNING RADIATION IS AVOIDED

BACKGROUND OF THE INVENTION

1. Field of the Invention

The present invention is directed to a method for scanning an examination subject with a CT apparatus having a radiation source that can be displaced around a system axis and that emits a ray bundle that strikes a detector system that supplies scan data on the basis of which two-dimensional scan images of the examination subject are determined in an image calculating device.

2. Description of the Prior Art

CT devices are known that have a ray source, for example an X-ray tube, that directs a collimated, pyramidal ray bundle through the examination subject, for example a patient, onto a detector system composed of a number of detector elements. The ray source and—dependent on the structure of the Ct apparatus—the detector system as well are attached on a gantry that rotates around the examination subject. A support mechanism for the examination subject can be displaced along the system axis relative to the gantry. The position proceeding at which the ray bundle penetrates the examination subject and the angle at which the ray bundle penetrates the examination subject are constantly varied as a result of the rotation of the gantry. Each detector element of the detector system struck by the radiation produces a signal that represents a measure of the overall transparency of the examination subject for the radiation emanating from the ray source on its path to the detector system. The set of output signals of the detector elements of the detector system that is acquired for a specific position of the ray source is referred to as projection. A scan comprises a set of projections that were acquired at various positions of the gantry and/or various positions of the bearing mechanism. The Ct apparatus registers a number of projections during a scan in order to be able to construct a two-dimensional tomogram of a slice of the examination subject. A number of slices can be simultaneously registered with a detector system constructed of an array of a number of rows and columns of detector elements.

Large volumes of the examination subject are usually registered with sequence scanning or spiral scanning. In sequence scanning, the data are registered during the rotary motion of the gantry while the examination subject is in a fixed position and planar slices are thus scanned. Between the scanning of successive slices, the examination subject is moved into a new position wherein the next slice can be scanned. This procedure is continued until all slices determined before the examination have been scanned. In a spiral scan, the gantry with the radiation source rotates continuously around the examination subject while the patient table and the gantry are continuously displaced relative to one another along a system axis. With reference to the examination subject, the ray source thus describes a spiral path until the volume defined before the examination has been scanned. Images of individual slices are then calculated from the spiral data acquired in this way.

CT apparatuses are also known wherein the X-ray power can be modulated during the rotation of the ray source around the examination subject for scanning an examination subject having a non-circular cross-section. When, for example, a patient lying on his/her back is scanned, then the path of the X-rays through the body of the patient usually is longer in the horizontal direction than in the vertical direction. If a modulation of the X-ray power is not possible, then this must be set such that the signal quality supplied for the projection having the longest path of the radiation through the body still suffices for the calculation of proper images. The X-ray power for all other projections is thus set according to the attenuation profile that is dependent on the angular position of the radiation source. Such a method is disclosed, for example, in German OS 198 06 063.

CT apparatuses are particularly utilized in the medical field. In addition to examination for purely diagnostic purposes, interventions (for example, biopsies, centesis) are being increasingly implemented with CT monitoring. During the intervention, the position of medical instruments required for the implementation of the intervention, for example a needle, thus can be continuously checked. Given an activated ray source and manual guidance of such a medical instrument by an examining person, body parts of the examining person, for example a hand, that are located in the region between the focus and the detector system are permeated by the ray bundle and can be exposed to unattenuated radiation.

U.S. Pat. No. 5,873,826 discloses an X-ray CT apparatus wherein the radiation power of the X-radiator can be reduced at times during the scan for reducing the radiation dose supplied to an examining person. The volume region for which this reduction is effective is defined before the scan and is marked by means of a light source during the scan.

SUMMARY OF THE INVENTION

An object of the present invention is to provide a method that allows a reduction of the radiation applied to an examining person with reference to the respectively actual position of a body part of the examining person that is susceptible to being located in the beam path.

This object is achieved in a method of the type initially described wherein parameters describing the position of a body part of an examining person situated in the beam path are determined by an analysis of registered scan images, and the radiation source is controlled dependent on the analysis result so that the radiation is reduced when the body part is located in the beam path.

The invention is characterized in that the radiation dose applied to the examining person is reduced without the examining person having to pre-define a volume region within the examination space before the beginning of the scan into which the examining person will introduce a body part—usually a hand—during the examination and within which he/she must confine movements if he/she would like to avoid exposure to an increased radiation dose. In accordance with the invention the presence (and absence) of a body part of the examining person in the beam path is quasi-continuously acquired in order—when the body part is present in the region—to determine parameters that describe the position of the body part in the beam path. This inventively ensues by means of an analysis of the registered scan images, i.e. of the two-dimensional CT images, wherein the body part, i.e., for example, the hand, is potentially visible. Dependent on this image analysis and the parameters describing the position that are acquired therefrom, the radiation source is then controlled such that the radiation is reduced precisely when the body part enters into the beam path and not only after it is completely in the beam path. The reduction is cancelled and the examination continued with the preset radiation dose as soon as the body part has in turn left the beam path or the radiation source was rotated farther to such an extent that the body part is no longer in the beam path.

As a result of this inventive scanning mode, describable as quasi in situ acquisition, a reduction is advantageously undertaken only when it is in fact required, so that potential quality losses in view of the registered images due to a radiation reduction can only occur in the images only wherein the radiation reduction is also absolutely necessary. Moreover, the constant analysis and thus position acquisition also make it possible to acquire every movement of the body part, and thus to continuously adapt and quasi readjust the region within which the radiation reduction must occur. The inventive method thus offers a high degree of safety for the examining person given simultaneous minimization of any potential qualitative disadvantages for the image exposure.

It is expedient when a volume region wherein the body part is located and wherein the radiation is reduced is determined on the basis of the parameters as analysis result. According to this embodiment of the invention, thus, a volume region with reference to the scan volume, that was scanned on the basis of the rotating radiation source and wherein the radiation reduction then ensues, is determined on the basis of the registered parameters that are acquired within the image analysis implemented with known analysis methods and analysis algorithms, for example as spatial coordinates.

In an embodiment of the inventive video images of the scan region swept by the radiation are registered with an acquisition system having at least one camera, and the parameters describing the position of the body part are analyzed, and the analysis result—possibly after previous determination of a volume region—is compared to the analysis result of the scan images, and the reduction of the radiation ensues dependent on the comparison. According to this embodiment of the invention, thus, the reduction ensues not only dependent on the scan image analysis but also dependent on the video images registered with the video acquisition system that shows a similar region a the scan images but in a qualitatively different form. These video images also are inventively analyzed with a suitable analysis method or algorithm with respect to the position parameters of the body part shown in the video images, and an analysis result comparable to the analysis result of the scan images is produced. Since the same body part—insofar as it is present—is shown in both types of image, comparable analysis results can be produced. Since the two images, however, were registered from different directions or show different views of the body part, there is the possibility of parameter correlation, i.e. a check can be carried out in this way to determine whether the overall analysis is correct. This ensues within the framework of the comparison.

Both parameters or parameter families can coincide or correlate with one another in the framework of the comparison, so that the analysis result of the video image confirms the analysis result of the scan image, or vice versa. Additionally, of course, there is also the possibility that the analysis results differ and the comparison clearly yields a difference. Different versions of the method are possible in this case.

Given different analysis results, in accordance with the invention, the analysis result of the scan images can have priority in view of the further control of the ray source, i.e. the further control ensues primarily dependent on the analysis result of the scan image. The information that the analysis results differ, however, is important in order to check ex post facto the extent to which the analysis methods correctly process the respective task, i.e. to what extent they correctly analyze the respective image. Since the scan image usually shows the body part significantly closer and sharper contrasts or contours can usually also be seen in this image, it is expedient to weight the analysis result of the scan image as priority or reference. Of course, it is also possible to either readjust the scan method or, respectively, the corresponding scan algorithm forming the basis of the video image scan according to the difference during the analysis, or to develop or adapt it in order to compensate the analysis differences. This, of course, alternatively can occur subsequently.

In another alternative of the method, given different analysis results in the framework of the comparison, the two analysis results are computationally linked with one another for forming the analysis result, insofar as the parameters allow a computational linking and can be mathematically correlated with one another. For example, averages can be formed, etc. The comparison result computationally formed as a result then forms the basis for the control of the ray source.

In a third alternative, given different analysis results and dependent on the nature and/or extent of the difference, an analysis result is selected to form the basis of the control of the ray source and this has a parameter-specific tolerance range, such as a volume region-specific tolerance range, allocated to it that is taken into consideration in the control of the radiation source. In this embodiment of the invention, thus, an analysis result to be employed with priority is not predetermined, but on the contrary, is selectable. A suitable tolerance range that can be defined dependent on the difference is allocated to it.

As described, it is expedient in any case when, given different analysis results, the analysis method on which the analysis of the video images is based is adaptively modified in order to eliminate the differences. For example, the algorithm is modified somewhat in the framework of this adaptive matching. The adaptation, of course, is dependent on the analysis method employed. Analysis methods for analyzing images that, in particular, are present in digital form are well-known.

As parameters, the x and y-coordinates of one or more characteristic points of the body part can be inventively determined in the respective image plane. It is expedient to define a number of points in terms of their coordinates, for example the left and right and upper and lower edges of the body part, for example, of the hand, in order to exactly acquire the contour of the body part in this way and thus to be able to exactly define the volume region. Further, the position of one or more characteristic points of the body part along the system axis as a z-coordinate can be defined as a parameter. This is also possible in the video images, when a second video camera is employed that generates a video image having an image plane lying in the system axis. Further, the angular range of the segment of the radiation plane illuminated by the moving radiation source can be defined as a parameter. The determination of the angular range is based on an analysis of the characteristic points that define the position of the entry and the exit of the body part into or out of the ray bundle, the angular range being the angle between these two points around which the focus of the ray source rotates.

As already described, it is expedient when the scan images and, if present, the video images are continuously analyzed and compared as warranted. Movements can be acquired in this way. Of course, periodic analysis and comparison is also possible. Movements also can be acquired in this case, whereby the time offset until an initiated movement is acquired is dependent on the length of the period between two analyses.

For reduction of the radiation, the radiation power can be temporarily reduced in a first embodiment of the invention, this ensuing either by varying the current of the radiation source or by means of an introduced local filter that partially absorbs the radiation. Alternatively, the reduction of the radiation can ensue by reducing the cross-section of the ray bundle using a suitable diaphragm device that is part of the radiation source or is allocated to it.

A probability calculation for determining parameters describing a movement of the body part can ensue continuously or periodically on the basis of parameters that describe the position and are acquired by analyzing the time-successively registered scan and/or video images. The result of the determination is processed together with the subsequently newly determined analysis result. In this embodiment of the invention, thus, analysis results that were already registered earlier are subjected to a probability calculation for advance calculation of a movement that is already occurring or has already been initiated and, of course, calculation of its direction as well. Such a result then can be considered as well in the further analysis of newly registered images.

In addition to the inventive method, the invention is also directed to a computed tomography apparatus suitable for the implementation of the method, having a ray source that is displaceable around a system axis and which emits a ray bundle that strikes a detector system that supplies scan data on the basis of which two-dimensional scan images of the examination subject are determined in an image calculating device, an analysis device for analyzing the two-dimensional scan images for determining parameters that describe the position of a body part of an examining person located in the beam path, and a control device for controlling the ray source dependent on the analysis result such that the radiation is reduced when the body part is located in the beam path.

Further, a recognition device can be provided that has at least one camera for generating video images of the scan region swept by the radiation, with the video images being analyzed in the analysis device for determining parameters that describe the position of the body part, and wherein the analysis device is fashioned for comparing the analysis result—possibly after previous determination of corresponding volume regions—to the analysis result of the scan images. The reduction of the radiation then ensues dependent on the comparison.

In an embodiment of the inventive CT system, the analysis device, which can make the analysis based on different analysis methods or analysis algorithms customized to the respective images, can be fashioned for determining, as the parameters, the x and y-coordinates of one or more characteristic points of the body part in the respective image plane and/or for determining the position of one or more characteristic points of the body part along the system axis as a z-coordinate and/or for determining the angular range of the radiation plane irradiated by the moving ray source. The recognition device can also have multiple video cameras at different positions dependent on which parameters are determined.

The analysis device itself can be fashioned for the continuous or periodic analysis of the scan images and, if present, the video images and comparison as warranted. In the framework of the comparison, the analysis device can implement a computational linking of two different results for forming the analysis result. Alternatively, the analysis device—given different analysis results—can be fashioned for selecting an analysis result to form the basis of the control and for allocating a parameter-specific or volume region-specific tolerance range that is to be taken into consideration in the control of the ray source. The respective selection and allocation can ensue dependent on the type and/or degree of the difference. Finally, the analysis device—given different analysis results—can be fashioned for the automatic adaptation of the analysis method underlying the analysis of the video images. Under certain circumstances, however, it is also conceivable that the video image analysis serves as reference vis a vis the scan image analysis and has priority, so that the scan image analysis method or, respectively, the corresponding algorithm can also be adaptively matched.

DESCRIPTION OF THE DRAWINGS

FIG. 1 is a schematic illustration and block diagram of a computed tomography apparatus constructed and operating in accordance with the present invention, with the apparatus being shown both in an end elevation FIG. 2 shows a portion of the computed tomography apparatus of FIG. 1, with the apparatus shown in a plan view, partly in section.

DESCRIPTION OF THE PREFERRED EMBODIMENTS

FIGS. 1 and 2 show an inventive computed tomography apparatus 1 in the form of a schematic drawing, with a front view of the CT apparatus in FIG. 1 and a plan view of the CT apparatus 1, partly in section, in FIG. 2 for illustrating the various camera positions.

The CT apparatus has a ray source 2, for example an X-ray tube, that directs a collimated, pyramidal ray bundle 3 through the examination subject 4, for example a patient, onto a radiation detector 5. The ray source 2 and, as a rule, the radiation detector 5 as well, are attached to a gantry (not referenced in detail) that rotates around the examination subject. The examination subject lies on a support mechanism, for example a patient table 6, that can be displaced relative to the gantry along the system axis, which proceeds in the plane of the drawing in the front view according to the left part of the illustration of the CT apparatus 1. The position proceeding from which the ray bundle 3 penetrates the examination subject 4 and the angle at which the ray bundle penetrates the examination subject 4 are constantly varied as a result of the rotation of the gantry. The ray bundle 3 is dimensioned relatively narrow, so that a narrow, limited image plane 7 can be scanned. The overall space irradiated or scanned during a rotation of the ray source 2 is called the scan volume.

Upon irradiation, the radiation detector 5 supplies image signals that represent a measure for the overall transparency of the examination subject 4 for the radiation emitted by the ray source 2 on its path to the radiation detector. The radiation detector 5 is composed of a number of individual detector elements (pixels), each of which supplies an output signal. The set of output signals of all defector elements that is acquired for a specific position of the ray source 2 is referred to as a two-dimensional projection. A scan comprises a complete set of projections that were acquired at various positions of the gantry and/or of the bearing mechanism. The CT apparatus 1 registers a number of projections during a scan in order to be able to construct a two-dimensional tomogram of a slice of the examination subject in the image plane 7.

The signals delivered by the radiation detector 5 are forwarded to a control device 8 that contains an image calculating device (not shown in detail) wherein the two-dimensional, individual projections are calculated and a two-dimensional scan image of the scan plane is determined therefrom.

In an intervention, for example a biopsy or a centesis with CT monitoring the examining person 10 works in the image plane 7 with a body part 11, for example a hand or arm, and is also exposed to radiation given a rotation of the ray source 2. The body part 11 is visible in the two-dimensional scan image since, as stated, it is located in the image plane. The scan image is analyzed in the analysis device 9 to determine whether a body part is shown in the image, and, if so, parameters that describe the position of the body part 11 are analyzed and identified. By this procedure a characterization is ultimately obtained regarding where the body part 11 is situated with reference to the rotary path of the X-ray tube. When the body part 11 enters into the beam path or the ray bundle 3 and exits therefrom can then be exactly determined. Since the exact position is known, the ray source 2 can then be controlled via the control device 8, to which these parameters in the analysis device 9 are forwarded, so that the radiation is reduced when the body part 11 enters the beam path until the exit of the body part, whereupon the radiation is returned to the prescribed intensity or power. A position-dependent modulation of the ray source or of the radiation thus ensues in order to designationally reduce the radiation when the body part of the examining person is irradiated.

As also can be seen from FIG. 2, a recognition system 12 having four separate video cameras 13 in the illustrated embodiment is also provided, the cameras 13 being arranged at different positions. Each video camera 13 supplies its own video images that are likewise forwarded to the analysis device 9. A separate analysis of these video images occurs in the analysis device 9 in order to determine whether the body part 11 is shown in the video images with reference to the position of the scanned image plane 7. When this is the case, the video image-specific parameters that describe the position of the body part are also determined here. The analysis results are then compared to the analysis result of the scan image analysis. When the two analysis results coincide, the comparison result is also forwarded to the control device 8 here, which correspondingly controlling the ray source 2. When, however, the analysis results do not agree, then, for example, a computational linking can ensue in the analysis device 9, for example for forming the average of the corresponding parameters that, for example, are registered as x, y and z-coordinates, and the like. The comparison result determined therefrom then serves as the basis, for example, for the calculation of a volume region in which the hand is located and wherein the radiation is to be reduced, and also serves for the control of the ray source 2.

Given such differences, the analysis device 9 can implement an adaptive matching of the analysis method or of the underlying analysis algorithm for the video image analysis, so that an adaptive position recognition is also possible in the video image.

Another advantage of the acquisition of the relevant position data of a body part located in the scan image is that this body part is blanked out in the scan image that is output at the monitor during the intervention, so that this does not obstruct the view of the actual examination region.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method for scanning an examination subject in a computed tomography apparatus, comprising the steps of
   emitting a beam of penetrating radiation and displacing said beam around a system axis and around an examination subject attended by an examining person;
   detecting said radiation after passage through said examination subject with a detector system and generating scanned data dependent on the detected radiation;
   while said examination subject is attended by said examining person, generating two-dimensional scan images of said examination subject from said scanned data;
   analyzing said scan images to determine whether a body part of said examining person is situated in said beam; and
   controlling said radiation source dependent on said determination to reduce said radiation when said body part is located in said beam.

2. A method as claimed in claim 1 comprising identifying from said parameter a volume region wherein said body part is located, and controlling said radiation source to reduce said radiation in said volume region.

3. A method as claimed in claim 1 wherein said examination subject is located within a scan region scanned by said beam, and wherein determining said parameter describing said position of said body part by analyzing said scan images represents a first analysis result, and comprising the additional steps of:
   obtaining a video image of scan region while said examination subject is attended by said examining person;
   analyzing said video image to determine a parameter describing said position of said body part of said examining person, representing a second analysis result;
   comparing said first analysis result and said second analysis result to obtain a comparison result;
   and wherein the step of controlling said radiation source comprises controlling said radiation source dependent on said comparison result.

4. A method as claimed in claim 3 comprising, if said comparison result indicates a difference between said first analysis result and said second analysis result, assigning said first analysis result a higher priority than said second analysis result for controlling said radiation source.

5. A method as claimed in claim 3 comprising, if said comparison result indicates a difference between said first analysis result and said second analysis result, computationally linking said first analysis result and said second analysis result to obtain an overall analysis result, and controlling said radiation source dependent on said overall analysis result.

6. A method as claimed in claim 3 comprising designating a tolerance range for said parameter and, if said comparison result indicates a difference between said first analysis and said second analysis result, selecting one of said first analysis result and said second analysis result for use in controlling said radiation source for which said parameter is within said tolerance range.

7. A method as claimed in claim 3 wherein said analysis of said video image to obtain said second analysis result proceeds according to a video analysis procedure and, if said comparison result indicates a difference between said first analysis result and said second analysis result, adaptively modifying said video analysis procedure.

8. A method as claimed in claim 3 wherein the step of analyzing said scan images to obtain said parameter in said first analysis result comprises analyzing said scan images to determine, as said parameter in said analysis result, a coordinate set comprising an x-coordinate and a y-coordinate of at least one characteristic point of said body part in an image plane of said scan images, and wherein the step of analyzing said video images to obtain said parameter in said second analysis result comprises analyzing said video images to determine, as said parameter in said second analysis result, a coordinate set comprising an x-coordinate and a y-coordinate of said at least one characteristic point of said body part in said image plane of said scan images.

9. A method as claimed in claim 8 wherein the step of determining said coordinate set as said parameter in said first analysis result includes determining a position of said characteristic point of said body part along said system axis as a z-coordinate, and wherein the step of determining said coordinate set as said parameter in said second analysis result comprises determining said position of said characteristic point of said body part along said system axis as a z-coordinate.

10. A method as claimed in claim 3 comprising continuously an analyzing said scan images to determine said parameter in said first analysis result and continuously analyzing said video images to determine said parameter in said second analysis result.

11. A method as claimed in claim 3 comprising periodically analyzing said scan images to determine said parameter in said first analysis result and periodically analyzing said video images to determine said parameter in said second analysis result.

12. A method as claimed in claim 1 wherein the step of analyzing said scan images to obtain said parameter comprises analyzing said scan images to determine, as said parameter, a coordinate set comprising an x-coordinate and a y-coordinate of at least one characteristic point of said body part in an image plane of said scan images.

13. A method as claimed in claim 12 wherein the step of determining said coordinate set includes determining a position of said characteristic point of said body part along said system axis as a z-coordinate.

14. A method as claimed in claim 1 wherein the step of analyzing said scan images to determine said parameter comprises determining an angular range, as said parameter, of a segment of a radiation plane irradiated by said beam.

15. A method as claimed in claim 1 comprising continuously analyzing said scan images to determine said parameter.

16. A method as claimed in claim 1 comprising periodically analyzing said scan images to determine said parameter.

17. A method as claimed in claim 1 wherein the step of emitting radiation from said radiation source comprises emitting radiation from said radiation source with a radiation power, and wherein the step of controlling said radiation source comprises temporarily reducing said radiation power.

18. A method as claimed in claim 17 wherein the step of reducing said radiation power comprises varying a current used to operates said radiation source.

19. A method as claimed in claim 17 wherein the step of reducing said radiation power comprises introducing a radiation-absorbing filter into said beam for partially absorbing said radiation in said beam.

20. A method as claimed in claim 17 wherein said beam has a cross-section, and wherein the step of reducing said radiation power comprises reducing said cross-section of said beam.

21. A method as claimed in claim 1 wherein said scan images are successively calculated, and wherein the step of analyzing said scan images to determine said parameter comprises repeatedly analyzing the successively calculated scan images to determine said parameter in each of said successive scan images as an indication of movement of said body part, and wherein the step of controlling said radiation source comprises controlling said radiation source dependent on said movement.

22. A computed tomography apparatus comprising:
an X-ray source which emits a beam of penetrating radiation;
an arrangement adapted for displacing said beam around a system axis and around an examination subject attended by an examining person;
a radiation detector disposed to detect said radiation after passage through said examination subject, said radiation detector generating scanned data dependent on the detected radiation;
an image computer for, while said examination subject is attended by said examining person, generating two-dimensional scan images of said examination subject from said scanned data;
an analysis device for analyzing said scan images to determine whether a body part of said examining person is situated in said beam; and
a control device connected to said analysis device for controlling said radiation source dependent on said determination to reduce said radiation when said body part is located in said beam.

23. A computed tomography apparatus as claimed in claim 22 wherein said analysis device identifies from said parameter a volume region wherein said body part is located, and wherein said control device controls said radiation source to reduce said radiation in said volume region.

24. A computed tomography apparatus as claimed in claim 22 wherein said examination subject is located within a scan region scanned by said beam, and wherein said analysis device determines said parameter describing said position of said body part by analyzing said scan images as a first analysis result, and further comprising at least one video camera which obtains a video image of scan region while said examination subject is attended by said examining person, and wherein said analysis device analyzes said video image to determine a parameter describing said position of said body part of said examining person, as a second analysis result, and compares said first analysis result and said second analysis result to obtain a comparison result, and wherein said control device controls said radiation source dependent on said comparison result.

25. A computed tomography apparatus as claimed in claim 24 wherein said control device, if said comparison result indicates a difference between said first analysis result and said second analysis result, assigns said first analysis result a higher priority than said second analysis result for controlling said radiation source.

26. A computed tomography apparatus as claimed in claim 24 wherein said control device, if said comparison result indicates a difference between said first analysis result and said second analysis result, computationally links said first analysis result and said second analysis result to obtain an overall analysis result, and controlling said radiation source dependent on said overall analysis result.

27. A computed tomography apparatus as claimed in claim 24 wherein said control device designates a tolerance range for said parameter and, if said comparison result indicates a difference between said first analysis and said second analysis result, selects one of said first analysis result and said second analysis result for use in controlling said radiation source for which said parameter is within said tolerance range.

28. A computed tomography apparatus as claimed in claim 24 wherein said analysis device analyzes said video image to obtain said second analysis result proceeds according to a video analysis procedure and, if said comparison result indicates a difference between said first analysis result and said second analysis result, adaptively modifies said video analysis procedure.

29. A computed tomography apparatus as claimed in claim 24 wherein said analysis unit analyzes said scan images to determine, as said parameter in said first analysis result, a coordinate set comprising an x-coordinate and a y-coordinate of at least one characteristic point of said body part in an image plane of said scan images, and analyzes said video image to determine, as said parameter in said second analysis result, a coordinate set comprising an x-coordinate and a y-coordinate of said at least one characteristic point of said body part in said image plane of said scan images.

30. A computed tomography apparatus as claimed in claim 29 wherein said analysis device also determines a position of said characteristic point along said system axis as a z-coordinate in said first analysis result, and also determines a position of said characteristic point of said body part along said system axis as a z-coordinate in said second analysis result.

31. A computed tomography apparatus as claimed in claim 24 wherein said analysis device continuously analyzes said scan images to determine said parameter in said first analysis result and continuously analyzes said video images to determine said parameter in said second analysis result.

32. A computed tomography apparatus as claimed in claim 24 wherein said analysis device periodically analyzes said scan images to determine said parameter in said first analysis result and periodically analyzes said video images to determine said parameter in said second analysis result.

33. A computed tomography apparatus as claimed in claim 22 wherein said analysis device analyzes said scan images to determine, as said parameter, a coordinate set comprising an x-coordinate and a y-coordinate of at least one characteristic point of said body part in an image plane of said scan images.

34. A computed tomography apparatus as claimed in claim 33 wherein said analysis device also determines said coordinate set includes determining a position of said characteristic point of said body part along said system axis as a z-coordinate.

35. A computed tomography apparatus as claimed in claim 22 wherein said analysis device analyzes said scan images to determine said parameter by determining an angular range, as said parameter, of a segment of a radiation plane irradiated by said beam.

36. A computed tomography apparatus as claimed in claim 22 wherein said analysis device continuously analyzes said scan images to determine said parameter.

37. A computed tomography apparatus as claimed in claim 22 wherein said analysis device periodically analyzes said scan images to determine said parameter.

38. A computed tomography apparatus as claimed in claim 22 wherein said radiation source emits said radiation with a radiation power, and wherein said control device controls said radiation source by temporarily reducing said radiation power.

39. A computed tomography apparatus as claimed in claim 38 wherein the control device reduces said radiation power by varying a current used to operate said radiation source.

40. A computed tomography apparatus as claimed in claim 38 further comprising a radiation-absorbing filter and wherein the control device reduces said radiation power by introducing said radiation-absorbing filter into said beam for partially absorbing said radiation in said beam.

41. A computed tomography apparatus as claimed in claim 38 wherein said beam has a cross-section, and wherein said control device reduces said radiation power by reducing said cross-section of said beam.

42. A computed tomography apparatus as claimed in claim 22 wherein said image computer successively calculates said scan images, and wherein said analysis device analyzes said scan images to determine said parameter by repeatedly analyzing the successively calculated scan images to determine said parameter in each of said successive scan images as an indication of movement of said body part, and wherein said control device controls said radiation source dependent on said movement.

* * * * *